United States Patent [19]

Coster et al.

[11] 4,055,799

[45] Oct. 25, 1977

[54] METHOD OF AND DEVICE FOR MEASURING ELASTIC AND DI-ELECTRIC PROPERTIES OF THE DIAPHRAGM OF LIVING CELLS

[75] Inventors: Hans Coster, New South Wales, Australia; Günter Pilwat; Ulrich Zimmermann, both of Julich, Germany

[73] Assignee: Kernforschungsanlage Julich Gesellschaft mit beschrankter Haftung, Julich, Germany

[21] Appl. No.: 651,337

[22] Filed: Jan. 22, 1976

[30] Foreign Application Priority Data

Jan. 23, 1975 Germany .......................... 2502621

[51] Int. Cl.$^2$ .......................................... G01N 27/00
[52] U.S. Cl. ......................... 324/71 R; 128/2.1 R; 204/195 B; 23/230 B; 195/103.5 R; 195/127
[58] Field of Search ................. 324/71 R, 65 R; 128/2.1 R, 2.1 Z, 2.1 E; 204/195 B; 23/230 B; 195/103.5 R, 127

[56] References Cited

U.S. PATENT DOCUMENTS

| 3,560,754 | 2/1971 | Kamentsky | 324/71 R X |
| 3,665,302 | 5/1972 | Lees et al. | 324/71 R X |
| 3,772,593 | 11/1973 | Sidhu | 324/71 R X |

Primary Examiner—Rudolph V. Rolinec
Assistant Examiner—Vincent J. Sunderdick
Attorney, Agent, or Firm—Walter Becker

[57] ABSTRACT

A method of and device for ascertaining elastic and di-electric properties of the diaphragm of individual living cells of living beings or of the diaphragms of such living cells in a physiological liquid in suspension or of such living cells in an association in the form of a layer. One or more of such cells or one or more layers of such cells is or are introduced into a physiological liquid which has a temperature of between 0° and 40° C and which is electrically conductive and forms an electrolyte solution. The cell, cells or layer of cells are located between two electrodes in such a way that the flow lines of an electric field provided between the two electrodes penetrate the diaphragm of the cell, cells or layer of cells introduced into the electrolyte solution. Thereupon a succession of voltage pulses with a constant pulse duration of from 1 μs and 10 ms is applied to the electrodes and the amplitude of the voltage pulses between 100 mV and 5V is increased until at the obtainment of the break-down voltage the resulting current pulses greatly increase. The break-down voltage will then be measured by means of two measuring electrodes.

5 Claims, 3 Drawing Figures

METHOD OF AND DEVICE FOR MEASURING ELASTIC AND DI-ELECTRIC PROPERTIES OF THE DIAPHRAGM OF LIVING CELLS

The present invention relates to a method of and a device for measuring elastic and di-electric properties of the diaphragm of individual living cells of living beings. In processes which occur in the cells of living beings which may be cells of an animal or of plant living beings or of cells of micro-organisms, for instance processes in which substances move into the diaphragm of cells or through the diaphragm of cells into the interior thereof, the character of the diaphragm of the cells plays a decisive role. Therefore, there is an endeavor to determine the character or buildup of the diaphragm. Also for judging the effect of foreign matters which are conveyed to the body of a living being onto the diaphragm of such cells, the quality, character or nature of the diaphragm of such cells is of great importance. Such investigations are important for instance for determining the effect of pharmaceutical substances or of the effect of poisons or other substances in concentrations harmful to the cells or also of the influence of diseases onto the diaphragm of living cells. While it is known that the functional capability of the diaphragm of living cells for the processes occurring in the cells is determined by elastic and di-electric properties of the diaphragm of the cells, and that a change in these properties shows a change of the behavior of the cells during the processes occurring in the cells, it has, in spite of strenuous efforts in this direction, heretofore been impossible to obtain by a process which can be carried out in a simple manner, an indication about the elastic and di-electric properties of the diaphragm of the cell and thus about the functional capability of cells for the above mentioned processes. It was rather necessary heretofore, for investigating the structure of the diaphragm of living cells of living beings to employ technically complicated and expensive methods which cannot be employed in an economic manner. Thus, for instance, the thickness of the diaphragm is measured by X-raying the cells or by electro-microscopically investigating the cells. Also the closeness of the molecules in the diaphragm of living cells of living beings is investigated by magnetic excitation of the nuclear spin of the molecules as well as the electron resonance signal of the free electron of a radical introduced into the diaphragm is measured. While in this way indications concerning the change in the diaphragm structure are possible, the elastic properties of the diaphragm of living cells are, however, not ascertainable in this manner.

It is, therefore, an object of the present invention to provide a method for ascertaining elastic and di-electric properties of the diaphragm of individual living cells of living beings or of the diaphragms of living cells of living beings, which living cells are present in a physiological liquid in a condition of suspension, which process will make it possible in a technically simple and economic manner to ascertain structrual changes of the diaphragm of living cells of living beings in order to recognize influences acting upon the diaphragm of the cell or cells.

It is a further object of this invention to provide a method which will furnish an indication of the structural buildup of the diaphragm of cells of living beings in order thereby in combination with the ascertainment of possible structural changes in the diaphragm of living cells of living beings due to the effect of foreign matter passed into the diaphragm or of other matter present in the cells in a concentration harmful to the cells, or in view of diseases, to obtain an indication concerning the functional capability for living processes occurring in the cells.

It is a further object of this invention to provide a device for carrying out the method set forth above.

These and other objects and advantages of the invention will appear more clearly from the following specification in connection with the accompanying drawings, in which.

Figure 1:
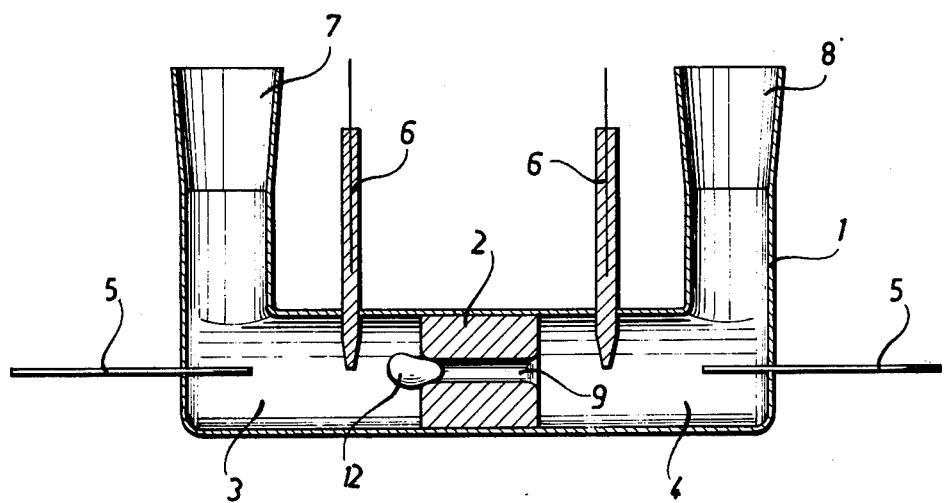
FIG. 1 illustrates a longitudinal section through a container according to the invention which is provided with a partition having a single opening designed as capillary.

For solving the above outlined problems, the invention starts with the finding that the permeability of a cell the diaphragm of which is moved into an electric voltage field is increased at a certain voltage which will henceforth be called the break-down voltage. The diaphragm of a living cell which in normal condition is, for all practical purposes, electrically non-conductive, becomes electrically conductive at said break-down voltage. This change in the properties can be ascertained by a measurable increase in the electric current flowing through the diaphragm. The invention furthermore starts with the finding that the magnitude of the break-down voltage at which the increase in the permeability occurs depends primarily on the di-electric properties of the diaphragm of the cell, on the elastic properties as well as on the thickness of the diaphragm of the cell, this interdependency is expressed by the formula $$(\text{Magnitude of the break-down voltage})^2 = \frac{0.3679 \times \delta_o \times y}{\epsilon \times \epsilon_o}$$

In this formula:
- $y$ represents the elasticity modulous of the diaphragm perpendicular to its surface
- $\delta_o$ represents the thickness of the diaphragm prior to applying the electric field
- $\epsilon$ represents the di-electricity constant for the diaphragm
- $\epsilon_o$ represents the di-electricity constant for the vacuum.

The magnitude of the break-down voltage thus represents a measuring number for these specific properties of the diaphragm of the cell.

The problem underlying the present invention is with a method of the above mentioned type solved according to the present invention by the fact that a single cell, a plurality of cells, or a plurality of individual cells, or one or more layers of cells are introduced into a physiological liquid having a temperature of from 0° to 40° C., conducting electric current, and forming an electrolyte solution, and that the cell, cells or layer of cells are so arranged between two electrodes that the stream lines or flow lines of an electric field created between the two electrodes penetrate the diaphragm of the cell introduced into the physiological liquid forming an electrolyte solution, or of the introduced cells, or of the cells of the introduced layer. Thereupon, a sequence of voltage pulses with a constant pulse duration of between 1 $\mu$s and 10 ms is employed, and the amplitude of the voltage pulses between 100 mV and 5 V is increased until at the obtainment of the break-down voltage, the resulting current pulses increase which can be measured by a current measuring device which is electrically connected to the electrodes. Thereupon, the break-down voltage is measured on two measuring electrodes which are arranged in a currentless condition at both sides of the cell provided between the electrodes, of cells arranged between the electrodes, or of the layer of cells arranged between the electrodes. Due to the fact that the voltage pulse-wise is applied to the diaphragm of the cell or cells, it will be assured in an advantageous manner that a destruction of the cell or of the cells due to heat influences will be prevented, which heat influences could occur when employing a constant voltage. In case that individual cells are to be investigated with a diameter of from 100 $\mu$m and a plurality of mm or cm, such as large algae cells, nerve axons or egg cells are to be investigated, it is suggested according to a modification of the method according to the invention expediently so to proceed that into the cell which is introduced into the physiological liquid forming the electrolyte solution there is introduced one of the two electrodes which are provided for emitting or receiving voltage and current pulses and which is designed as microelectrode and the tip of which has a diameter between 0.1 and 20 $\mu$m depending on the magnitude of the cell to the investigated. The voltage pulses are then applied between the micro-electrode and the second electrode extending into the liquid.

The modification of the method according to the invention according to which a micro-electrode is employed for measuring the break-down voltage, may also be employed with smaller cells for instance, with erythrocytes which have a diameter of approximately 3 $\mu$m. However, a further modification of the method according to the invention has proved particularly advantageous. This last mentioned method consists in that the cell introduced into the physiological liquid is drawn onto the opening which at a maximum has a dimension of the diameter of the cell and which is provided in a partition which in an electrically insulating manner separates from each other the electrodes provided for emitting and receiving voltage and current pulses as well as the measuring electrodes. As an alternative, the cells introduced into the physiological liquid are drawn onto openings which have as a maximum the dimensions of the diameter of the cells and are provided in a partition which separates in an electrically insulating manner the electrodes and the measuring electrodes provided for emitting and receiving voltage and current pulses, so that when applying an electric voltage to the two electrodes for emitting and receiving voltage and current pulses, the current or flow lines penetrating the opening or openings and pertaining to the generated electric field at the same time penetrate the diaphragm of the cell drawn onto the opening or the diaphragm of the cells drawn onto the openings. The diameter of the opening or openings in the partition is so dimensioned that the drawn-on cells clog up said opening or openings.

If a plurality of cells is to be investigated, as partition between the electrodes expediently a glass frit or a filter is employed in which the openings of the pores have dimensions which at a maximum equal the magnitude of the diameter of the cells. When practicing the method according to the invention, the cells present in suspended condition in the physiological liquid are drawn to one side of the partition of the glass frit or to the filter which wall or filter has said openings. The drawn-on cells will then clog up or close the openings of the pores of the glass frit or of the filter. This clogging up of the pore openings on one hand brings about an increase in the flow resistance for the liquid, which flow resistance is measurable by means of a manometer connected to the system. The said clog-up of the pore openings will on the other hand, due to the diaphragm of the sucked-on cell or cells — said diaphragm acting as electric insulation — bring about an increase in the electric resistance between the electrodes, which resistance is measurable by means of the device connected to the electrodes. Subsequently thereto, according to the method of the invention, the break-down voltage for the cell diaphragm is measured. With this modification of the method according to the invention in which simultaneously a plurality of cells are subjected to a measurement, a statistic mean value is obtained for the break-down voltage.

Since the increase in the permeability of the diaphragm of the cells which is effected when the break-down voltage is reached, and which occurs after a time varying according to the type of cells from one second to one minute during which no voltage pulses are applied to the electrodes, is, so to speak, healed again, the method according to the invention can thus with the same cells be repeated after a relatively short time.

If only a few cells are available for investigation, or if during investigations in which the diaphragm properties of individual cells are to be investigated, as partition for insulating the electrodes from each other there is provided a partition which has only one opening or instead of the opening has a capillary while its diameter is at a maximum equal to the diameter of the cell to be investigated. The method according to the invention is then carried out in a manner analogous to the measurement of the break-down voltage for a plurality of cells.

This modification of the method according to the invention according to which a single, a number, or a plurality of cells are drawn onto the opening or the openings in a wall or partition, is applicable for all cells of living beings which either already in their natural condition are suspended in a physiological liquid as for instance, erythrocytes or leukocytes in the blood or micro-organisms in their nutrition medium or which are adapted to be suspended in a physiological liquid by the application of corresponding methods and are thus held in suspension as individual cells in the liquid. This is the case, for instance, with tumor cells or with cells of plant organs which, for instance, by means of detergents or also complex formers such as ethyldiaminetetraacetic acid are adapted to be dissolved out of the compound of the cells.

If the method according to the invention is intended for measuring the break-down voltage of the diaphragm of cells in a layer which may consist of up to 20 layers of cells, for instance, the leaf of a plant or the section of a cell fabric of an organ, the layer of cells is expediently connected to the opening or the openings in the partition which separates in an electrically insulating manner the electrodes from each other. Such connection may be effected by pressing said layer of cells against the opening or openings by means of a rubber ring. The dimensions of the openings are expediently adapted to the magnitude of the layer of the cells.

The method according to the invention is advantageously applicable to the ascertainment of changes in the diaphragm of cells of living beings, which changes may be caused by diseases or by foreign matters or by matters in a concentration harmful for the cells. Changes in the diaphragm structure of the cells of living beings, which are caused by diseases as is the case for instance with erythrocytes diseased by sickle cell anemia, or is the case with tissue cells diseased by cancer such as tumor cells or the like, are ascertainable in a simple manner by employing the method according to the invention. By employing the method according to the invention, it is furthermore possible likewise in a similar simple manner to ascertain changes in the diaphragm structure of the cells of living beings which have been caused by foreign matter for instance poisonous substances or other ecologically caused harmful substances, or also by medicine. The method according to the invention is therefore also employed in an advantageous manner for recognizing such influences which change the diaphragm of the cells, for instance, for an early recognition of changes of the diaphragm of cells of living beings as they may be caused by diseases. The advantageous employment of the method according to the invention also includes the ascertainment of changes of the diaphragm of cells of living beings, for instance, changes in the diaphragm of the cells of sweet water and sea water algae whereby the influence of ecological harmful substances upon the ecology of water can be ascertained. The employment of the method according to the invention for ascertaining changes in the diaphragm of cells is additionally possible with microorganisms for instance, bacteria or yeast cells, in an advantageous manner. Thus, for instance, the required dosing of substance intended for killing bacteria can be ascertained in a simple manner.

A very advantageous device for practicing the method according to the invention is characterized primarily in that a container of electrically non-conductive material such as glass or the like, is by means of a partition divided in two chambers with one electrode each arranged in said chambers for emitting and receiving voltage and current pulses, and with a measuring electrode each arranged in the chambers for measuring the break-down voltage, and with at least one opening or conduit connection for feeding physiological electrolyte solution and for introducing the cell, the cells, or the layer of cells into one of the chambers. If one, more or a plurality of cells are introduced into one of the chambers of said container, the partition is provided with a number of openings corresponding to the number of cells, with said openings having a diameter the maximum of which corresponds to the dimensions of the cell or cells and with a conduit connection extending into the other chamber for drawing in electrolyte solution. If a layer of cells is introduced into the container, the partition serving as supporting wall for the layer of cells is provided with one or more of openings adapted to the magnitude of the layer of cells. The two electrodes intended for emitting the voltage and current pulses are connected to a device for producing voltage pulses of variable amplitude up to 5 V and adapted to generate a variable pulse duration from about 1 μs to 10 ms, and are furthermore provided with a device for measuring the amplitude of the current pulses occurring in view of the voltage pulses applied to the electrodes, while the two measuring electrodes provided for measuring the break-down voltage are provided with a device for amplifying measuring voltages.

Referrring now to the drawings in detail, the container 1 comprises a partition 2 by means of which the container 1 is sub-divided into a chamber 3 and a chamber 4. In each of these two chambers 3 and 4 there is arranged an electrode 5 each for emitting voltage and current pulses, and a measuring electrode 6 each for measuring the potential difference of voltages on both sides of the partition 2. The measuring electrodes comprise a chlorinated silver wire arranged in a micropipette which is filled with a 2 N—KCl— solution which was solidified by the addition of a certain quantity of the solidifier known under the name Agar-Agar. The chamber 3 is provided with a connection 7 for the supply of a physiological liquid in which are present the cell or the cells of living beings in suspended condition. The chamber 4 has a connection 8 for the supply of electrolyte liquid, which connection at the same time serves as conduit connection for a suction device (not shown) for drawing the cells onto the partition 2. The partition 2 in the container 1 illustrated in FIG. 1, which container is provided for measuring the break-down voltage in an individual cell, is provided with an opening 9 designed as capillary. The partition 2 of the container 1 in FIG. 2, which container serves for measuring the break-down voltage on a plurality of cells, comprises a diaphragm filter which has a plurality of openings 9, rests on a screen plate 10 as supporting wall for the diaphragm filter, said diaphragm filter being pressed against said plate 10 by means of a rubber ring 11 and a clamping device not illustrated in the drawing. In both FIGS. 1 and 2, the cells 12 to be investigated are illustrated in a position in which they will be after they have been drawn onto the partition. As will be evident from the drawing, the cells when drawn onto the partition block the openings 9 so that the flow lines which penetrate the openings 9 and pertain to an electric field created between the electrodes 5 simultaneously penetrate the diaphragm of the drawn-on cell or cells.

Figure 2:
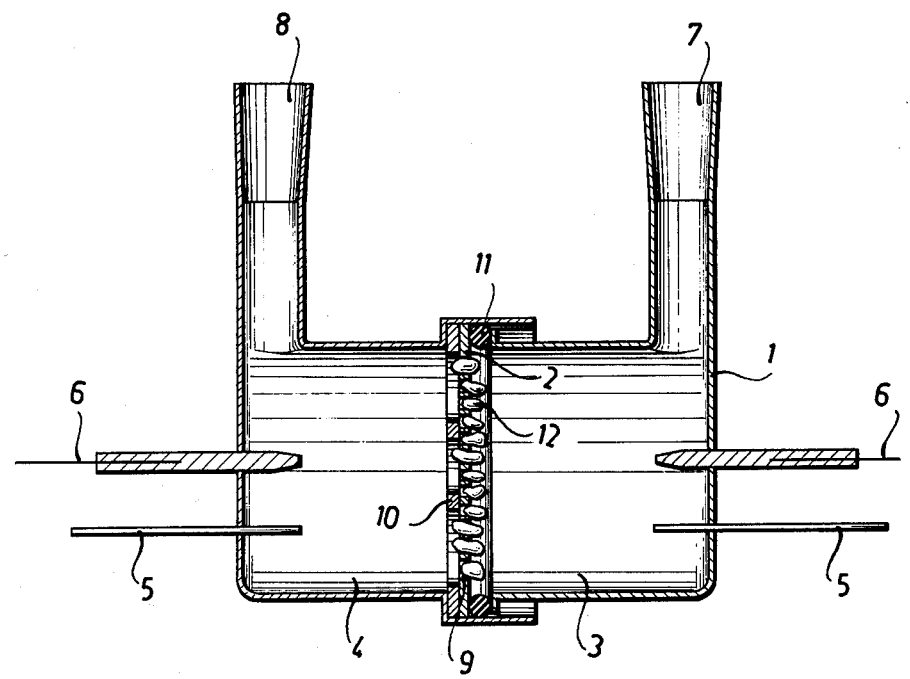
FIG. 2 represents a longitudinal section through a container according to the invention with a partition having a plurality of openings.

If a layer of cells is to be investigated, the layer instead of the diaphragm filter illustrated in FIG. 2 is pressed against the screen plate 10 by means of the rubber ring 11.

Figure 3:
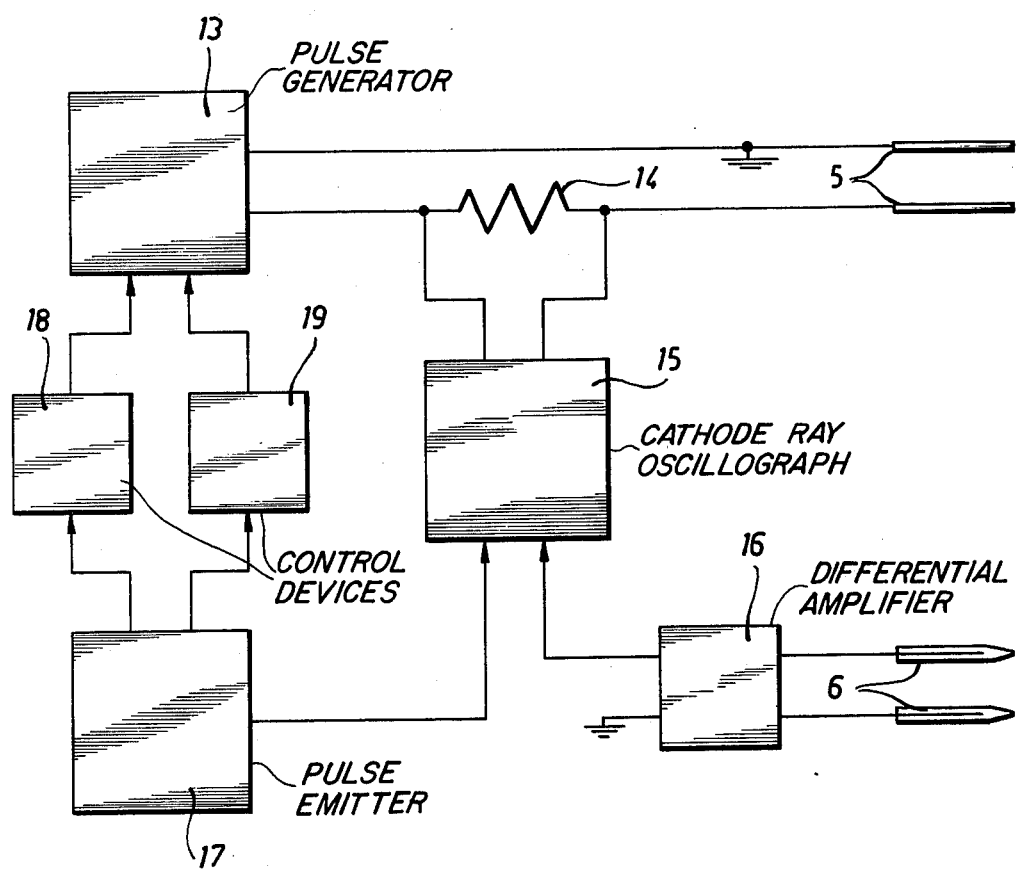
FIG. 3 represents a diagrammatic illustration of a device according to the invention for generating voltage pulses and for measuring the amplitude of the resulting current pulses and also shows a device for measuring the break-down voltage.

As will be seen from FIG. 3, the electrodes 5 provided for emitting and receiving voltage pulses are connected to a pulse generator 13 which has a lower starting resistance. The pulse generator 13 generates (not illustrated in the drawing) a sequence of constant voltage pulses of pulse duration between 1 μs and 10 ms. In one of the two connecting lines between the electrode 5 and the pulse generator 13 there is provided a resistor 14. This resistor serves for ascertaining by voltage tap the current which flows through the electrodes 5. The voltage drop measured on the resistor 14 is for purposes of indication conveyed to a cathode ray oscillograph 15 which is designed as storage oscillograph.

As will be evident from FIG. 3, the two measuring electrodes 6 provided for measuring the break-down voltage of the diaphragm of the cell or cells connected to a differential amplifier 16 which has a high input impedance. The voltage values amplified in the differential amplifier 16 are likewise conveyed to the cathode ray oscillograph 15 and together with the current pulses measured as voltage drop through the resistor 14 are indicated on the indicating screen of the cathode ray oscillograph.

As will likewise be seen from FIG. 3, for purposes of establishing the pulse sequence, there is provided a pulse emitter 17 which for sequentially indicating the voltage pulses emitted by the pulse generator 13 and thus also of the resulting current pulses as well as of the pulses of the potential values measured by the measuring electrodes 6, is directly connected to the cathode ray oscillograph 15 and through a control device 18 is connected to the pulse generator 13. By means of the control device 18, the voltage pulses emitted by the pulse generator 13 are delayed so long that the voltage pulses and the resulting current pulses as well as the pulses of the potential values measured by the measuring electrodes 6 are indicated on the indicating screen of the cathode ray oscillograph 15 in a sequence corresponding to their timewise sequence. By means of the control device 19, through which the pulse emitter 17 is likewise connected with the pulse generator 13, the amplitude of the voltage pulses emitted by the pulse generator 13 is controlled and is increased in conformity with a predetermined mathematical interrelationship.

EXAMPLE 1

A quantity of 1 ml erythrocytes was introduced into a physiological solution comprising 100 ml of a 139 mM/1 sodium chloride and 15 mM/1 sodium phosphate and having a temperature of about 20° C., the pH value of said solution amounting to 7.4. The thus formed suspension in which the erythrocytes were in suspension was then subdivided into 10 approximately equal partial quantities of which 9 partial quantities were each time intermixed with a different quantity (indicated in the first column of Table 1) of benzyl alcohol. For purposes of measuring the break-down voltage which was carried out by means of a device according to FIGS. 2 and 3, the ten partial quantities comprising a different quantity of benzyl alcohol were respectively individually introduced into the chamber 3 of the container 1 of FIG. 2, the partition of which consisted of a diaphragm filter with a pore diameter of 2 μm. Subsequently, an under-pressure of about 0.6 atm was employed or created in chamber 4 until the pores of the filters were blocked by erythrocytes which blocking was ascertained by means of a manometer connected to the suction line.

Thereupon, every 30 seconds, a voltage pulse of a pulse duration of about 25 μs was applied to the electrodes 5, while the amplitude of the voltage pulses was respectively increased by 300 mV. In this way, the height of the break-down voltage was roughly ascertained in a first measurement. In a second measurement, which was carried out after a waiting period of about 5 minutes within which the cells healed again, the amplitude of the voltage pulses was respectively increased within the region of the height of the break-down voltage by from 50 to 100 mV. In this connection, for the diaphragm of the cells which were present in the partial solutions which contained a different concentration of benzyl alcohol, the break-down voltage listed in the second column of Table 1 was measured. In the third column of Table 1, there are listed the corresponding values for the percentage change of the measured break-down voltage with reference to the value measured for the solutions listed in the first line of Table 1.

TABLE 1

| Concentration of Benzyl Alcohol in mM/l | Break-down Voltage in Volts | Relative Change in the Break-down Voltage in % |
|---|---|---|
| 0 | 1.42 | 0 |
| 1 | 1.42 | 0 |
| 10 | 1.38 | − 3 |
| 30 | 1.36 | − 4 |
| 50 | 1.31 | − 8 |
| 70 | 1.18 | −17 |
| 90 | 1.12 | −21 |
| 100 | 1.02 | −28 |
| 110 | 0.99 | −30 |
| 120 | 0.89 | −37 |

EXAMPLE 2

In a manner analogous to that of Example 1, the break-down voltage for the diaphragms of erythrocytes was measured, which diaphragm differed by their content in cholesterine. The cholesterine content of the diaphragm of cells which was ascertained by biochemical analysis is indicated in the first column of Table 2 as the qualitative change with regard to a partial quantity of erythrocytes with normal cholesterine which partial quantity is listed in the first line of Table 2. The measured break-down voltages are indicated in the second column of Table 2. In the third column of Table 2 there are listed the percentage changes of the break-down voltages with regard to the break-down voltage measured for the first solution.

TABLE 2

| Cholesterine content of the Diaphragm of Erythrocytes | Break-down Voltage in Volts | Relative Change in the Break-down Voltage in % |
|---|---|---|
| Normal | 1.39 | 0 |
| Slight decrease | 1.63 | + 17.3 |
| High decrease | 1.66 | + 19.4 |
| Slight enrichment | 1.42 | + 2.2 |
| Strong enrichment | 1.19 | − 14.4 |

EXAMPLE 3

Bacteria of the type escherichia coli B 163 were introduced into a physiological liquid which had a temperature of 20° C. and which contained 30 mMol/1 KC1, 1 mMol/a MgCl$_2$, 90 mMol/1 Na$_2$HPO$_4$, 30 mMol/1 NaH$_2$OP$_4$, 15 mMol/1 (NH$_4$)$_2$SO$_4$, 0.5% glucose and 100 mg/1 histodine and leucine. After approximately 6 hours, a partial quantity was withdrawn from the thus formed solution in which it was found that the bacteria were at this time growing logarithmicly, and the breaddown voltage of the diaphragm of the cells of the bacteria present in these partial quantities was determined in a manner analogous to the Example 1. The pore diameter of the pores of the employed diaphragm filter amounted to 0.45 μm. The measured break-down voltage amounted to 1.06 V. After further ten hours, another partial quantity was withdrawn from the solution in which it was found that the bacteria were at this time in a stationary growth. The measured break-down voltage of the diaphragm of the cells of the bacteria present in this partial quantity amounted to 1.29 V.

EXAMPLE 4

An electrode designed as micro-electrode and consisting of platinum-iridium, the tip of which at a diameter of 1 μm and the shank of which had a diameter of about 5 μm, was introduced into an algae cell with a diameter of about 0.5 cm of the algae type valonia utrikularis which was present in a bath of Mediterranean sea water which bath was tempered to 20° C. This introduction was effected by introducing said electrode into a micropipette of glass which was previously introduced into the algae cell. The diameter of said micro-pipette was within the range of from 5 to 7 μm. Outside the cell, a further electrode of pure nickel was arranged in a sea water bath. Through these two electrodes, voltage pulses with a pulse duration of 1 ms were emitted in time intervals of about 5 seconds while the amplitude of the voltage pulses was respectively increased by 100 mV. The break-down voltage was measured by two micro-pipettes of glass which were designed as measuring electrodes and were filled with 2 N—KCl— solution. One of said micro-pipettes was introduced into the algae cell, whereas the other micro-pipette extended directly into the sea water solution. The electrodes provided for emitting and receiving voltage pulses as well as the measuring electrodes were connected to a device illustrated in FIG. 3. The measured break-down voltage of the algae cell amounted to 0.85 V.

It is, of course, to be understood that the present invention is, by no means, limited to the specific examples set forth above but also comprises any modifications within the scope of the appended claims.

What we claim is:

1. A method of ascertaining elastic and di-electric properties of the diaphragm of individual living cells of living beings and of the diaphragms of living cells of living beings which living cells are in suspension in a physiological liquid or in an association as a layer of living cells of living beings, which includes the steps of: introducing any member of the group consisting of an individual cell, a plurality of individual cells, a number of individual cells, a layer of cells, and a plurality of layers of cells, into a physiological liquid which has a temperature within the range of from 0° to 40° C and which is electrically conductive and forms an electrolyte solution, locating said member between two electrodes in such a manner that the flow lines of an electric field provided between said two electrodes penetrates the diaphragm of said member introduced into said physiological liquid forming said electrolyte solution, applying to said electrodes a sequence of voltage pulses with a constant pulse duration of from 1 μs to 10 ms, increasing the amplitude of said voltage pulses between 100 mV and 5 V until at the obtainment of the break-down voltage the resulting measurable current pulses greatly increase, and measuring the break-down voltage on two measuring electrodes arranged currentless on both sides of said member provided between said electrodes.

2. A method according to claim 1, which includes the steps of: drawing the cell introduced into the physiological liquid onto an opening provided in a wall electrically insulating from each other the measuring electrodes and the electrodes provided for emitting and receiving voltage and current pulses, said opening having a diameter not exceeding the diameter of said cell, so that when applying an electric voltage to said electrodes the flow lines of the thus generated electric field which penetrate said opening also at the same time penetrate the diaphragm of the cell drawn onto said opening.

3. A method according to claim 2, which includes the steps of: drawing the cells introduced into the physiological liquid onto openings having a diameter not exceeding the diameters of said cells and being provided in a wall electrically insulating from each other the measuring electrodes and the electrodes provided for receiving and emitting voltage and current pulses so that when applying an electric voltage to said electrodes the flow lines of the thus generated electric field which penetrate said openings also at the same time penetrate the diaphragms of the cells drawn onto said openings.

4. A device for ascertaining elastic and di-electric properties of the diaphragm of individual living cells of living beings and of the diaphragms of living cells of living beings with the living cells in suspension in a physiological liquid or in an association as a layer of living cells of living beings, which includes: container means of electrically non-conductive material, partition means arranged in said container means and dividing same into two chambers, two electrodes respectively arranged in said chambers for emitting and receiving voltage and current pulses, two measuring electrodes respectively arranged in said chambers for measuring the break-down voltage, said container means being provided with inlet means for supplying physiological electrolyte solution and for the introductin of a cell, and cells and a layer of cells into one of said chambers, said partition means being provided with passage means therethrough corresponding in number to the number of cells to be introduced into said one chamber and having a diameter not exceeding the diameter of the cells in said one of said two chambers, first means electrically connected to said two electrodes for generating voltage pulses of variable amplitude up to about 5 V and of variable pulse duration of from about 1 μs and 10 ms, second means electrically connected to said two electrodes for emitting voltage and current pulses for measuring the amplitude of the current pulses occurring in view of the voltage pulses applied to said electrodes, and third means electrically connected to said measuring electrodes for amplifying and measuring voltages.

5. A device according to claim 4, in which said container means is of glass.

* * * * *